(12) United States Patent
Cichocki et al.

(10) Patent No.: US 8,062,437 B2
(45) Date of Patent: Nov. 22, 2011

(54) THERMAL FORMING OF REFRACTORY ALLOY SURGICAL NEEDLES AND FIXTURE AND APPARATUS

(75) Inventors: Frank R. Cichocki, Easton, PA (US);
Thomas Nering, Holland Township, NJ (US); David Demarest, Parsippany, NJ (US)

(73) Assignee: Ethicon, Inc., Somerville, NJ (US)

( * ) Notice: Subject to any disclaimer, the term of this patent is extended or adjusted under 35 U.S.C. 154(b) by 941 days.

(21) Appl. No.: 11/756,679

(22) Filed: Jun. 1, 2007

(65) Prior Publication Data

US 2008/0295927 A1    Dec. 4, 2008

(51) Int. Cl.
*C21D 1/00* (2006.01)
(52) U.S. Cl. .............................. 148/567; 372/1; 425/174
(58) Field of Classification Search .................. 148/567; 425/174; 372/1
See application file for complete search history.

(56) References Cited

U.S. PATENT DOCUMENTS

| | | | |
|---|---|---|---|
| 1,906,101 A | 4/1933 | Rickey et al. |
| 2,666,721 A | 1/1954 | Bechtold et al. |
| 3,573,903 A | 4/1971 | Delgrosso |
| 3,686,041 A | 8/1972 | Lee |
| 4,501,312 A | 2/1985 | Matsutani |
| 5,026,520 A | 6/1991 | Bhowal et al. |
| 5,411,613 A | 5/1995 | Rizk et al. |
| 5,415,707 A | 5/1995 | Bendel et al. |
| 6,077,369 A | 6/2000 | Kusano et al. |
| 7,001,472 B2 | 2/2006 | Collier et al. |
| 7,014,722 B1 | 3/2006 | Arimoto et al. |
| 2001/0001401 A1 | 5/2001 | Vladimir |
| 2005/0044922 A1 | 3/2005 | Bogart |

FOREIGN PATENT DOCUMENTS

| | | |
|---|---|---|
| DE | 3620718 A1 | 12/1987 |
| EP | 0646352 A1 | 4/1995 |
| EP | 0646352 B2 | 6/1998 |
| FR | 1415939 A | 10/1965 |
| FR | 1472637 A | 3/1967 |
| GB | 145739 A | 1/1921 |
| JP | 54155959 A | 12/1979 |

OTHER PUBLICATIONS

Peter L. Raffo "Yielding and Fracture in Tungsten and Tungsten-Rhenium Alloys", NASA Technical Note (NASA TN D-4567) May 1968.
Erik Lassner and Wolf-Dieter, "Tungsten," Kluwer Academic/Plenum Publishers, NY, p258, 1999.

*Primary Examiner* — Emily M. Le
*Assistant Examiner* — Weiping Zhu
(74) *Attorney, Agent, or Firm* — E. Richard Skula (57) ABSTRACT

A method of thermal forming of refractory alloy suture needles is disclosed. Needle blanks made from refractory alloys are used to form surgical needles, which are heated to a temperature above the ductile to brittle transition temperature but below the recrystallization temperature of the refractory alloy. The heated needle blanks are then mechanically formed into a surgical needle. A Fixture and an apparatus for forming refractory alloy surgical needles using this method are also disclosed.

22 Claims, 7 Drawing Sheets

THERMAL FORMING OF REFRACTORY ALLOY SURGICAL NEEDLES AND FIXTURE AND APPARATUS

This patent application is related to commonly-assigned patent application Ser. No. 11/756,668 entitled "Thermal Forming of Refractory Alloy Surgical Needles" filed on even-date herewith and incorporated by reference.

FIELD OF ART

The field of art to which this invention pertains is surgical needles, in particular, methods of thermally forming refractory alloy suture needles.

BACKGROUND OF THE INVENTION

Surgical needles are well known in the surgical arts. Typically the surgical needles are mounted to sutures, and used in a variety of surgical procedures for approximating tissue. It is important that the surgical needles function under a variety of conditions encountered by surgeons when performing procedures on patients. Surgical needles can be used for delicate surgical procedures with relatively soft and fragile tissues such as liver or lung surgery and for more robust procedures involving harder and tougher tissues such as ophthalmic, plastic, or coronary artery bypass graft surgery. Surgical needles are also used in various orthopaedic surgical procedures. Surgical needles must be able to penetrate tissue rapidly and efficiently with minimal surgeon insertion force and minimal tissue trauma. It is particularly important that the surgical needle maintain its structural integrity through multiple cycles while tissue is being approximated by the surgeon.

Surgical needles may be made from a variety of materials that have the required strength and manufacturability properties. Examples of these materials include various grades of stainless steel including, 420, 455, 4310 and various grades of specialty martensitic-aged steels including ETHALLOY (Ethicon, Inc., Somerville, N.J.). Although needles made from such conventional materials are capable of adequate performance, there is a constant search for surgical needles having improved properties that will benefit both the surgeon and the patient. Certain refractory metals offer unique properties such as exceptional stiffness and strength that impart desirable handling characteristics to suture needles. However, the room temperature formability of many refractory alloys is limited and often substantially less than the formability of other metals typically used in the manufacture of suture needles. Difficulties may thus arise in the manufacture of refractory alloy surgical needles as numerous steps in a conventional manufacturing process require substantial material ductility. Suture needle bodies are often press-formed or coined to exhibit flattened sides to facilitate grasping and needle orientation within the suture needle drivers. Needle bodies formed to exhibit flattened sides may also impart modest improvements in strength and stiffness to the suture needle. Needle points also may be coined to produce cutting edges desirable for the penetration of certain tissues. Furthermore, needles are commonly curved into a variety of arcuate configurations, for example, ¼, ⅜, or ½ circle designs, in order to facilitate certain surgical procedures. The surgical needles must be processed during manufacturing to provide for the mounting of surgical sutures. One way of mounting sutures to a surgical needle is to drill a blind bore hole into the proximal end of the needle to receive the end of a surgical suture. For channel mounted sutures, as opposed to sutures mounted in a drilled bore hole in the proximal end of the needle, needle channels are typically coined or stamped into the proximal end of the suture needle. In either type of mounting configuration, the proximal ends of the needles are typically swaged to maintain the suture end in the channel or the bore hole.

The forming of refractory alloys into suture needle materials has not been extensively investigated. Conventional needle forming methods typically cannot be used with refractory alloys. For example, it is known to use a method of forming a suture receiving hole in steel needles by pressing a perforating tool into the base of suture needle while the needle material is heated to a temperature close to the melting temperature, Tm, between the hot forming and casting temperature of the alloy. This method is deficient for use on refractory metals for several reasons. If an alloy is taken to a temperature near the melting point of the alloy, recrystallization of the alloy is a distinct likelihood. Indeed recrystallization commonly occurs at much lower temperatures, for many alloys around 0.4 Tm. If refractory metals are heated to near their melting point, recrystallization of the work hardened microstructure occurs and the alloy can be expected to lose essential properties and even exhibit brittle characteristics at room temperature due to the effect of microstructural changes on the ductile to brittle transition temperature, DBTT. Secondly, such a process is applicable to oxidation resistant alloys, however, this is not the case for refractory alloys (especially those in the W—Re binary system) as these alloys will readily oxidize at temperatures far below their melting points.

The previously described needle forming methods may impart substantial stresses to the needle material, and if the material exhibits insufficient ductility, cracking and or splitting of the suture needle may occur. Many refractory alloys exhibit ductile to brittle transition temperatures (DBTT) above room temperature, and consequently the ability to plastically deform these refractory alloys in the various surgical needle forming operations is substantially limited. However, once above the DBTT, plastic deformability of the refractory alloys increases substantially. Excessively high temperatures may however lead to the recrystallization and growth of the grain structure of the alloy, leading to a substantial change in properties that may be deleterious to the performance of the suture needle.

Therefore, there is a need in this art for novel methods of manufacturing and forming refractory alloy suture needles.

BRIEF DISCLOSURE OF THE INVENTION

Accordingly, a novel method of thermal forming refractory alloy suture needles is disclosed. In the method, an alloy metal needle blank is provided. The needle blank is made from a refractory metal alloy. At least a section of the needle blank is heated to a temperature above the ductile to brittle transition temperature but below the re-crystallization temperature of the alloy. The heated needle blank is mechanically formed into a surgical needle.

Another aspect of the present invention is a fixture useful in the practice of the above-described process of the present invention to heat refractory metal alloys during a forming process. The fixture has an upper insulating member having a top side, a bottom side and a cavity extending up from the bottom side. The member has a die passage extending therethrough for receiving a die. There is a lower insulating member having a top side, a bottom side and a cavity extending down from the bottom side. The lower insulating member has a die passage extending therethrough for receiving a die. The fixture has an insulator block having a cavity and a pair of opposed needle slots. The insulator block has a passage extending therethrough for receiving at least one die. A heater element block mounted in the cavity of the insulator block. The heater element block has a longitudinal needle slot substantially in alignment with the opposed slots of the insulator block, and the heater element block has a die passage extending therethrough and intersecting the slot for receiving at least one die. And, the fixture has a radio frequency (RF) electromagnetic induction source member. The insulator block containing the heater element and the RF source member are mounted in the cavities between the upper and lower insulating members to form an inductive heating fixture such that there is a slot between the upper and lower insulating members in alignment with the opposed slots of the insulating block and the slot of the heater element block. In addition, the die passages of the lower insulating member, the insulating block, the heater element, and the upper insulating member are substantially in alignment.

Yet another aspect of the present invention is an apparatus for forming refractory alloy surgical needles. The apparatus has a frame. Mounted to the frame is a die press having at least one die and a slidable indexing fixture. The above-described inductive heating fixture is mounted to the frame in alignment with the die or dies of the die press.

These and other aspects of the present invention will become more apparent from following description and accompanying drawings.

DETAILED DESCRIPTION OF THE INVENTION

Using the novel thermal forming processes of the present invention, refractory alloys used in the manufacture of suture needles are heated to a temperature above their DBTT during the given forming operation to provide substantial plastic deformation, but below the recrystallization temperature of the alloy to prevent compromise of the suture needle properties. Several methods for the thermal treatment and forming of suture needle materials during needle forming operations are disclosed. Needles manufactured from refractory metal alloys treated using the novel thermal forming treatment processes of the present invention exhibit numerous potential improvements in needle performance including enhanced resistance to bending, pronounced I-beam (i.e., structural) and needle point designs that enhance strength, stiffness and penetration performance, improved ductility and toughness, and in situ coloration via surface oxidation.

The following terms used in present specification are defined to have the following meanings:

Ductile to Brittle Transition Temperature (DBTT)—Temperature above which a substantial improvement in ductility of the alloy occurs. Within this disclosure the DBTT is determined as the temperature at which the alloy exhibits at least 5% elongation to break in a simple tensile test.

Refractory Alloy—alloy comprised of one or more or the elements: W, Mo, Re, Os, Ir, Ta, Nb, Zr, Y that exhibit a DBTT above room temperature.

Recrystallization Temperature—Temperature at which new grains will form in the microstructure of the alloy.

Ductility—ability of an alloy to withstand plastic deformation without breaking.

Elongation to break—measurement of sample percent elongation in a simple tensile test, used to assess alloy ductility.

Simple Tension—tension applied in one dimension with other dimensions being unconstrained.

Thermal forming—plastic forming conducted on a heated work piece.

Needle Blank—elongate piece of wire, a portion of which is converted via a multitude of processes into the shape of a suture needle.

Yield Bending Moment—the amount of moment required to initiate plastic deformation during bend tests (ASTM standard F-1840-98a)

Bending Stiffness (Stiffness in Bending)—resistance to elastic deformation of a curved suture needle.

Elastic Deformation—deformation, strain, or displacement that is recoverable by removing the applied load I-beam Needle Body—any variety of needle body designs that incorporate flattened opposed sides (instead of an entirely rounded design)

Maximum Bending Moment—the greatest moment applied to needle during bend test (ASTM standard F-1840-98a)

Materials Properties—Properties of the material only, derived by testing in a manner in which needle shape and surface properties do not influence data. Examples include: Young's modulus, ultimate tensile strength (when tested in simple tension), and microhardness hardness.

Grain Structure—an assemblage of crystals that share a common atomic periodicity and together as a multitude comprise the needle material.

Dislocation—a line defect within a grain structure that manifests itself as a missing plane of atoms, that is commonly necessary to enable plastic deformation of metals at or near room temperature.

It should be noted the terms "surgical needle" and "suture needle" are used interchangeably herein.

The metal alloys useful in the practice of the present invention include conventionally known refractory metal alloys including: tungsten, tungsten-rhenium, tungsten-osmium, molybdenum, molybdenum-rhenium, molybdenum-zirconium-titanium, iridium, and the like.

Rhenium additions can substantially improve the ductility of W—Re alloys. Published results for arc melted W—Re alloys of varying Rhenium concentration are disclosed in NASA technical publication (NASA TN D-4567) entitled, "Yielding and Fracture in Tungsten and Tungsten-Rhenium Alloys". A tungsten 25% Rhenium alloy exhibited substantial elongation to break near room temperature whereas a pure tungsten sample exhibited no reportable elongation to break. Taking a closer look at the pure tungsten alloy, it was clear that a marked improvement in elongation to break occurred over the temperature range of 520 to 600K. Over this temperature range the alloy transitioned from brittle to ductile. A ductile to brittle transition temperature (DBTT) is often used to demarcate this transition in ductility, and while this nomenclature is the norm in the field of metallurgy, the actually transition in materials performance does not typically occur at a precise single temperature, but rather occurs over a range of temperatures in a polycrystalline sample. The breadth of this DBTT transition region may increase with Rhenium concentration, with high Rhenium alloys showing a gradual slope up in elongation to break with temperature as opposed to the more rapid change of the pure alloy. Nevertheless, it is clear that heat profoundly increases the ductility exhibited by W—Re alloys. According to this NASA report, for a W-25% Re alloy, the room temperature ductility approximately doubles at 500K and approximately quadruples at 700K. For convenience, the author of this NASA study chose the temperature at which the alloy exhibited 5% elongation to break as the ductile to brittle transition temperature (DBTT), or for the W-25% Re alloy, 350K. It should be noted that other factors such as alloy impurities, grain size, and work hardening history can also impact the onset temperature of ductile behavior (and the reported value of the DBTT).

Suture needles are conventionally and most typically formed from wire through a multitude of conventional process steps including: wire straightening, needle blank formation, point coining and/or point grinding, needle body forming, curving, suture receiving hole drilling, or channel forming, polishing, siliconization, and so on. The process steps may include one or more conventional mechanical, chemical, heat treatment, and/or electrical sub-processes. Suture needle forming operations often result in substantial plastic deformation of the needle material. Even alloys with high rhenium concentration exhibit limited plastic deformation with elongation to break values rarely exceeding 7% at room temperature and more commonly less than 5%. This lack of room temperature ductility can limit the shape and design of the suture needle. In particular, suture needles are typically formed to exhibit rectangular cross-sectional shapes in the body or mid-section of the needle. Such a rectangular cross-section facilitates grasping and control of the suture needle with needle holders in addition to imparting a modest increase in strength and stiffness. In order to form a rectangular cross-section, a series of conventional coining operations, by which the needle is partially flattened between two parallel opposing dies, is typically performed. These coining operations can result in deformation strains that exceed the fracture limits of the W—Re alloy at room temperature. Likewise, needle points are conventionally coined using various conventional dies and conventional coining processes and equipment. A variety of conventional point designs may be coined including but not limited to: taper point, cutting edge, or taper-cut varieties. Cutting edge needles generally provide the best tissue penetration performance with minimal tissue trauma. However, unlike taper point or taper cut needles that may be formed via a sequence of grinding processes, cutting edge needles of optimal design require point coining operations that subject the needle material to substantial deformational strains, and consequently cracks in the needle blank can occur if forming is conducted below the DBTT of a refractory alloy. In particular, cutting edge needles with radius hollow cutting edges, as described by Smith et. al in U.S. Pat. No. 5,797,961A, which is incorporated by reference, offer exceptional penetration performance with minimal tissue trauma, but in production must be preformed via a high deformation coining operation. Other cutting edge needle point designs for ophthalmic and micro surgery are similarly complex, and while offering exemplary tissue penetrating performance, also require high deformation coining operations to produce. Finally, channels may be conventionally formed in the proximal end of suture needles to facilitate suture attachment. This approach is particularly applicable to suture needles with wire diameters below ~0.006" that can be exceedingly difficult to mechanically drill or laser drill for the purposes of producing a suture receiving hole. Substantial plastic deformation commonly occurs during needle channel formation, and if a refractory alloy is formed at room temperature below its DBTT cracking will likely occur.

The novel processes of the present invention enhance the formability of refractory metal alloys such as the tungsten alloys for the purposes of producing suture needles. These novel thermal forming processes of the present invention provide that a metal alloy suture needle blank be elevated to a temperature, just prior to or during a forming operation, that exceeds the DBTT (where the DBTT is determined as the temperature at which the alloy exhibits at least 5% elongation to break in a tensile test) but wherein the temperature is less than the recrystallization temperature of the alloy (where the recrystallization temperature is defined for the purposes of this disclosure as any temperature that leads to the formation of new grains in the microstructure of the alloy, during said forming operation). It is important to prevent recrystallization of the alloy, as a recrystallized microstructure will typically exhibit lower tensile strength, and lower yield strength, both of which are adverse to the handling and performance characteristics of the suture needle. Moreover, recrystallization of refractory alloys, in particular tungsten alloys, often leads to the embrittlement of the alloy by further elevating the DBTT as a consequence of the elimination of dislocations that occurs during recrystallization.

While mechanical forming of a refractory metal suture needle blank at elevated temperature may be necessary to prevent fracture, it is not easily accomplished since equipment used in the manufacture of suture needles is expansive in nature employing several specialized forming stations that typically perform individual needle forming operations serially one after the other, and this equipment cannot be, as a whole, subjected to elevated temperature for long without destroying its function. This equipment is typically high speed precision equipment, and excessive heat could cause mechanical breakdowns of mechanical components. As such, heating of the refractory metal needle blank must be limited to a very small section of the equipment where heat resistant or water-cooled tooling can be used. Alternatively the heat used in forming the needle blanks must be managed, for example to be turned on and then turned off with precise timing to heat predominantly the needle and not the surrounding tooling and equipment. Alternatively, the tooling may be actuated in such a way to substantially limit the duration of its exposure to the thermal forming zone.

Alternate embodiments of methods of the present invention for thermal forming needles in situ to heat an alloy metal needle blank during or immediately prior to forming are illustrated in FIGS. 1-4, and described herein. These methods include, but are not limited to: 1) resistive needle heating, 2) forced gas needle heating, 3) element controlled needle heating, and 4) laser needle heating.

Figure 1A:
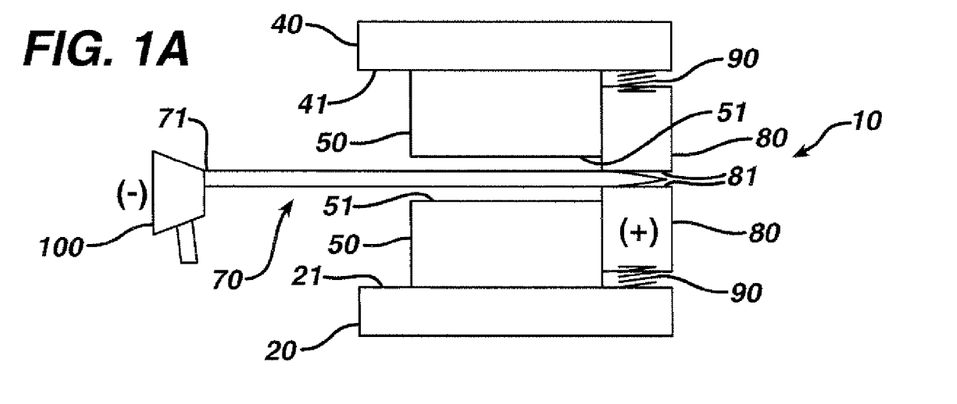
FIGS. 1A-C illustrate a schematic of a thermal forming process of the present invention utilizing resistive heating.
Figure 1B:
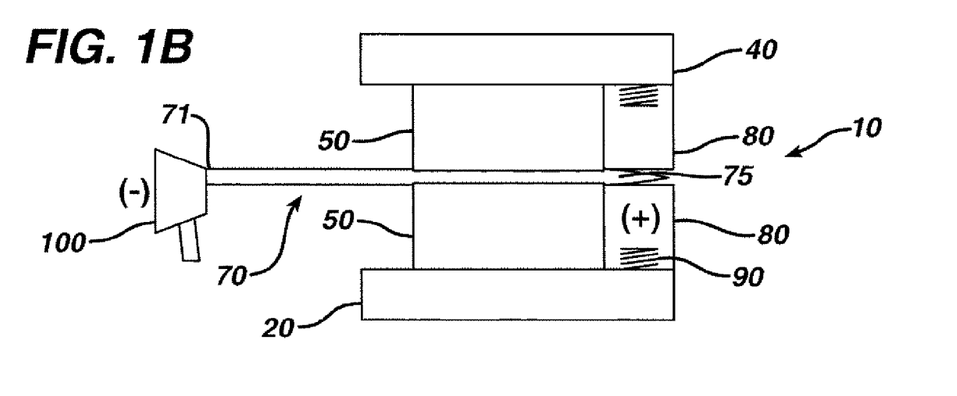
Figure 1C:
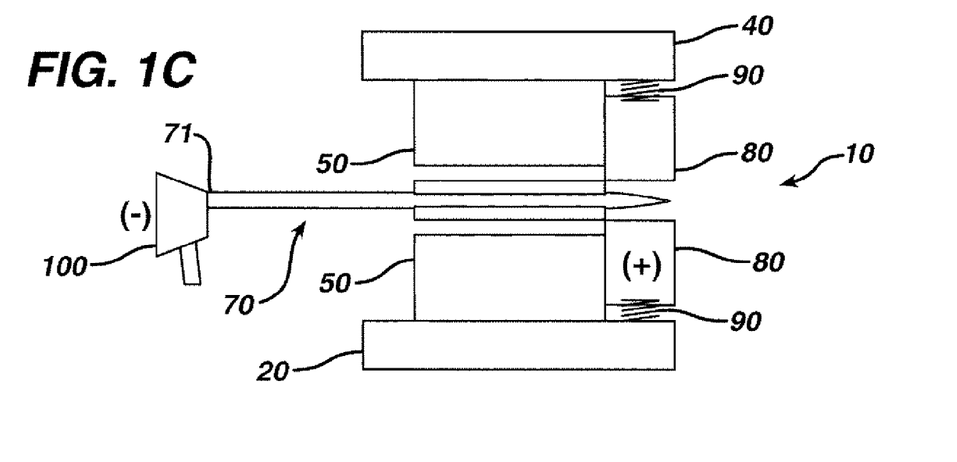

Referring first to FIGS. 1A-C, a resistive heating embodiment of the process of the present invention is illustrated. The forming die tool 10 is seen to have lower tool base 20 and upper moveable member 40. Mounted respectively to the inner surface 21 of tool base 20 and the inner surface 41 of moveable member 40 are the die members 50 each having inner contact surfaces 51 for engaging the metal alloy needle blank 70. The tool 10 is seen to have a pair of opposed electrodes 80 having contact surfaces 81. The electrodes 80 are moveably mounted via springs 90 to the tool base 20 and moveable member 40, respectively. An electrode 100 is mounted to the proximal end 71 of needle blank 70. In the resistive needle heating process, electrical contact is made across the needle blank from the distal end 75 of needle blank 70 via the electrodes 80 to the proximal end of the needle blank 71 via electrode 100 and current is passed through the needle blank 70 to resistively heat it to the temperature desired for the forming operation. Electrical contact can be made across the length of the needle blank 70 as the needle blank 70 enters the die 10 or as it closes, as seen in FIGS. 1A-C. Alternatively, current maybe passed through the thickness of the needle blank 70 in the section in which forming will occur. Various traditional materials may be used to form the conducting electrodes 80 (e.g. copper) used to make electrical contact and complete the electrical circuit to allow current to pass through the needle blank 70. Optionally, the die members 50 may be used to make electrical contact and conduct the current, as many of the conventional tools such as cemented carbide tools typically used employ a continuous metal binder phase of substantial conductivity. The dies and/or electrical contacts may be optionally liquid cooled to increase their performance and service life. The amount of current passed through the needle blanks 70 in the process of the present invention will be sufficient to effectively heat the needle blank 70 to above its DBTT without inducing recrystallization of the grain structure. The current will depend on wire diameter, composition of the refractory alloy, speed of the die closure, and other dynamic process factors, (and also upon electrical parameters such as voltage, frequency, etc.) but may typically be about 1.0 amp to about 20.0 amps, more typically about 1.0 amp to about 10.0 amps.

Figure 2A:
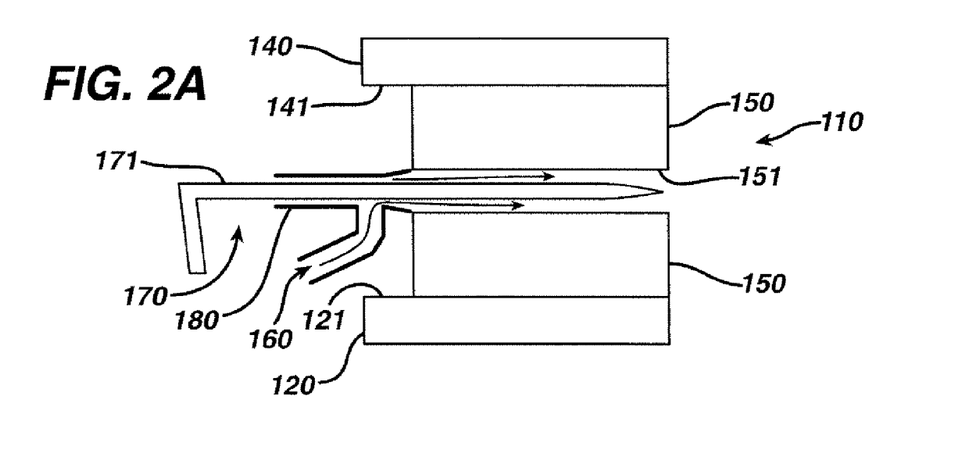
FIGS. 2A-C illustrate an alternate embodiment of the present invention for thermal forming needles from refractory alloys using a hot gas injection system.
Figure 2B:
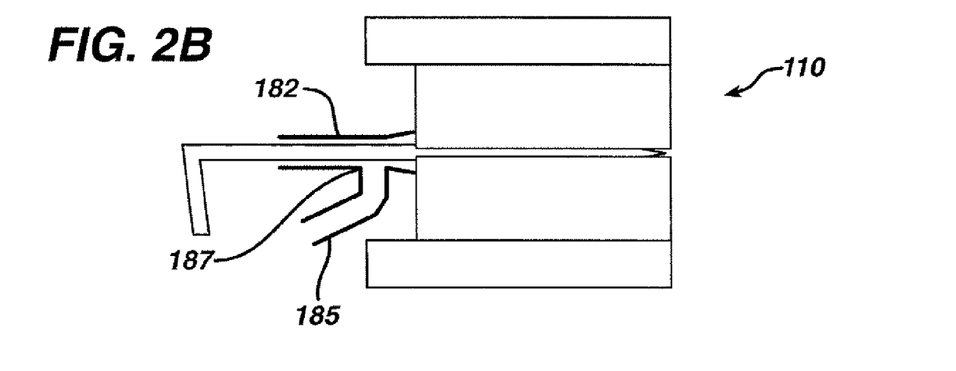
Figure 2C:
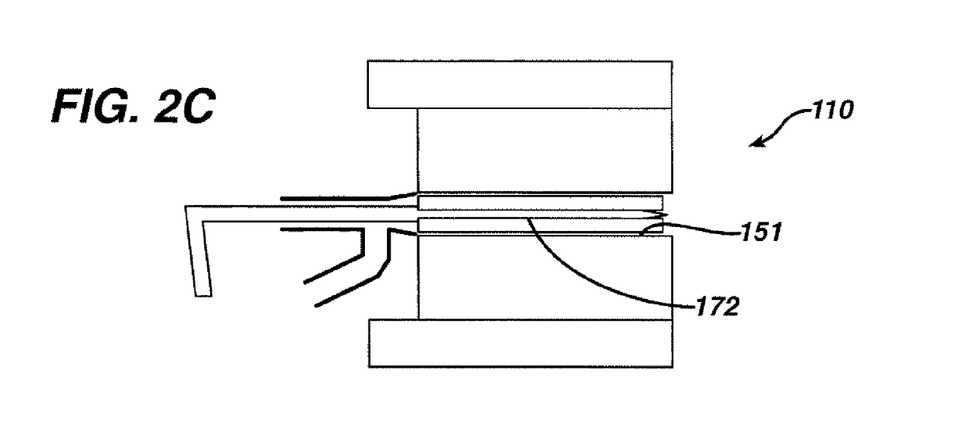

Another alternate embodiment of the process of the present invention using a forced gas thermal forming process is illustrated in FIGS. 2A-C. The forming die tool 110 is seen to have lower tool base 120 and upper moveable member 140. Mounted respectively to the inner surface 121 of tool base 120 and the inner surface 141 of moveable member 140 are the die members 150 each having inner contact surfaces 151 for engaging the metal alloy needle blank 170. With the forced gas method, a stream of hot air or hot gas 160 is directed via guide 180 along the path of the alloy needle blank 170 as it enters and while it is positioned within the die assembly 110 between opposed die members 150. The guide 180 is seen to have needle guide section 182 and gas pathway section 185 that intersect at junction 187. Since the needle blanks 170 are typically small in diameter (between ~1 and 60 mil) rapid convective heating of the needle blank 170 from the forced gas stream 160 may occur. As the needle blank 170 reaches a predetermined forming temperature, the dies 150 close and thermoform a segment 172 of the needle blank 170 to the prescribed shape, as seen in FIGS. 2a-c. The gas used to heat the suture needle may optionally be a shielding gas which would serve to prevent oxidation of the needle during the heating operation. Examples of the gases that can be used include argon, helium, hydrogen, nitrogen, neon, carbon dioxide/carbon monoxide, or mixtures thereof. The velocity of the gas stream and the temperature of the gas stream will be effective to sufficiently heat the refractory alloy above its DBTT while preventing recrystallization. The temperature of the needle during the thermoforming process will be sufficient to effectively enable plastic deformation required in the forming operation without cracking or splitting of the needle blank. The temperature will vary with the alloy selected to manufacture the needle blank. For a W—Re alloy needle blank the temperature will typically range from 100 to about 1900° C., more typically about 300 to about 1600° C., and preferably about 600 to about 1400° C.

Figure 3A:
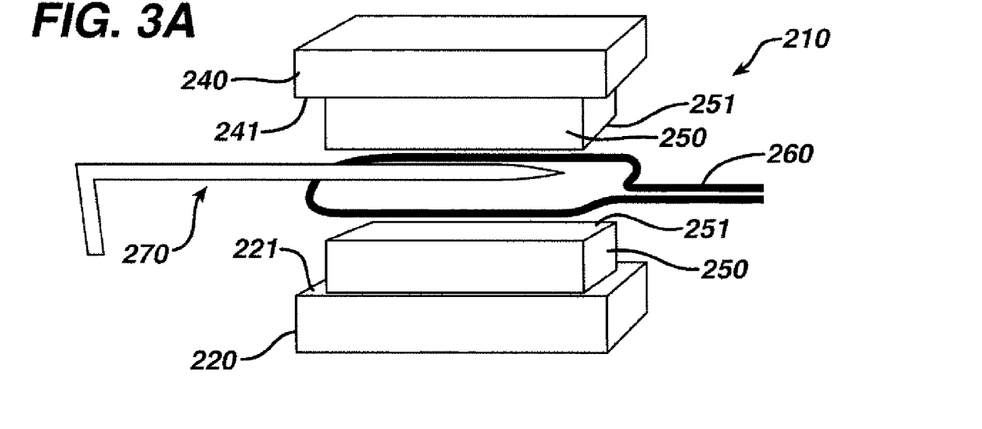
FIGS. 3A-C illustrate yet another alternate embodiment of the present invention for thermal forming of refractory alloy needles using a resistive heating element.
Figure 3B:
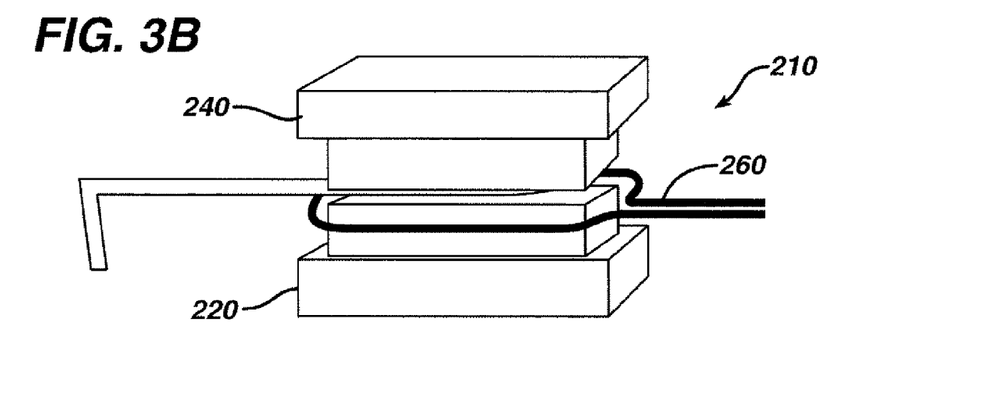
Figure 3C:
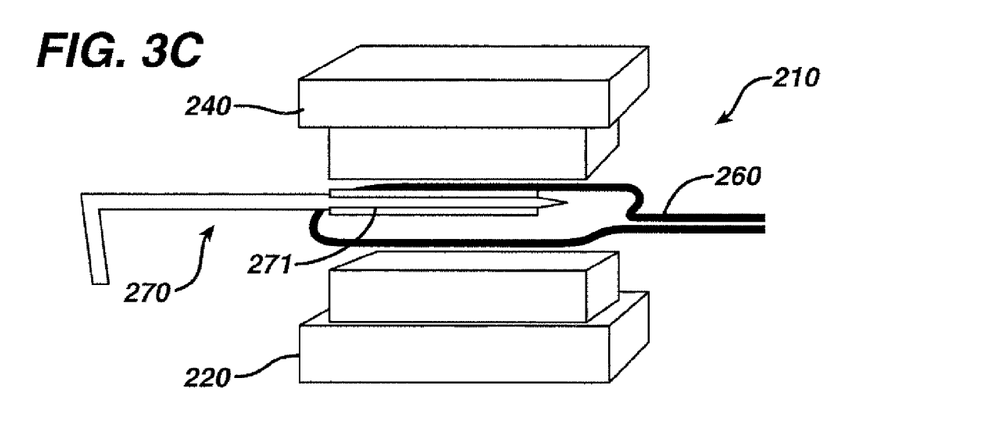

Still yet another embodiment of a thermal forming process of the present invention is illustrated in FIGS. 3A-C. The method utilizes a formed resistive heating element. The resistive element may be heated via direct contact to an electrical circuit designed to pass current through the heating element. Alternatively, the resistive heating element may be heated by inductively coupling to a radio frequency magnetic field that in turn induces an alternating current in the element to accomplish resistive heating. Either configuration generates radiant energy from the heating element to heat the suture needle. As seen in FIGS. 3A-C, the forming die tool 210 is seen to have lower tool base 220 and upper moveable member 240. Mounted respectively to the inner surface 221 of tool base 220 and the inner surface 241 of moveable member 240 are the die members 250 each having inner contact surfaces 251 for engaging the metal alloy needle blank 270. A resistive heating element 260 is seen positioned within and about the die assembly in such a way that the heating element 260 fits around the working zone of the die 210, while not interfering with the motion of the needle blank 270 as it enters and leaves the thermal forming zone, and also without interfering with the movement of the die members 250. The heating elements 260 may be electrically or electronically controlled to turn on and off at the appropriate times as the dies open and close to prevent excessive heating of the dies. As seen in FIGS. 3A-C, after the needle blank 270 is heated to a sufficiently effective temperature, the die members 240 engage the needle blank 270 to thermally form a section of the blank 271. Alternatively or in addition to time control of the heating elements, the dies and affected machine components may be optionally liquid cooled to prevent excessive thermal damage. Also, the dies may optionally retract away from the heating element to a position where the temperature does not cause degradation of the die material. As previously described, the heating elements may be of the type that provide radiant heat (as would be the case for standard resistively heated elements, infrared heating elements, and inductively coupled heating elements), or may be in the form of an induction coil wherein the induction coil produces radio frequency that couples directly with and inductively heats the needle blank. If an induction heating element is used, it may be advantageously designed to couple effectively with and heat the needle blank, but not couple with the surrounding dies. The desired temperatures will be those as previously described above for the other thermal heating and forming processes.

Although not illustrated, another thermal forming process of the present invention utilizes laser controlled needle heating. As the name implies, this embodiment uses a focused intense laser light beam to rapidly heat sections of the needle blank that require mechanical forming. One or more lasers may impinge upon the needle blank simultaneously to increase the length of the hot zone. The lasers may also be directed back and forth rapidly across the length of the needle that will be formed. Alternatively the needle may be rotated as the laser impinges to increase the heat-affected area.

It will be recognized that as the hot needle blank contacts the lower temperature dies, or as the source of the thermal energy is shut-off, the needle blank will have a tendency to begin to cool. As such, all of the thermal forming processes described above should be designed in such a way that the actual forming operation that results in plastic deformation of the needle material occurs rapidly in comparison to the rate at which the needle blank cools.

Figure 4:
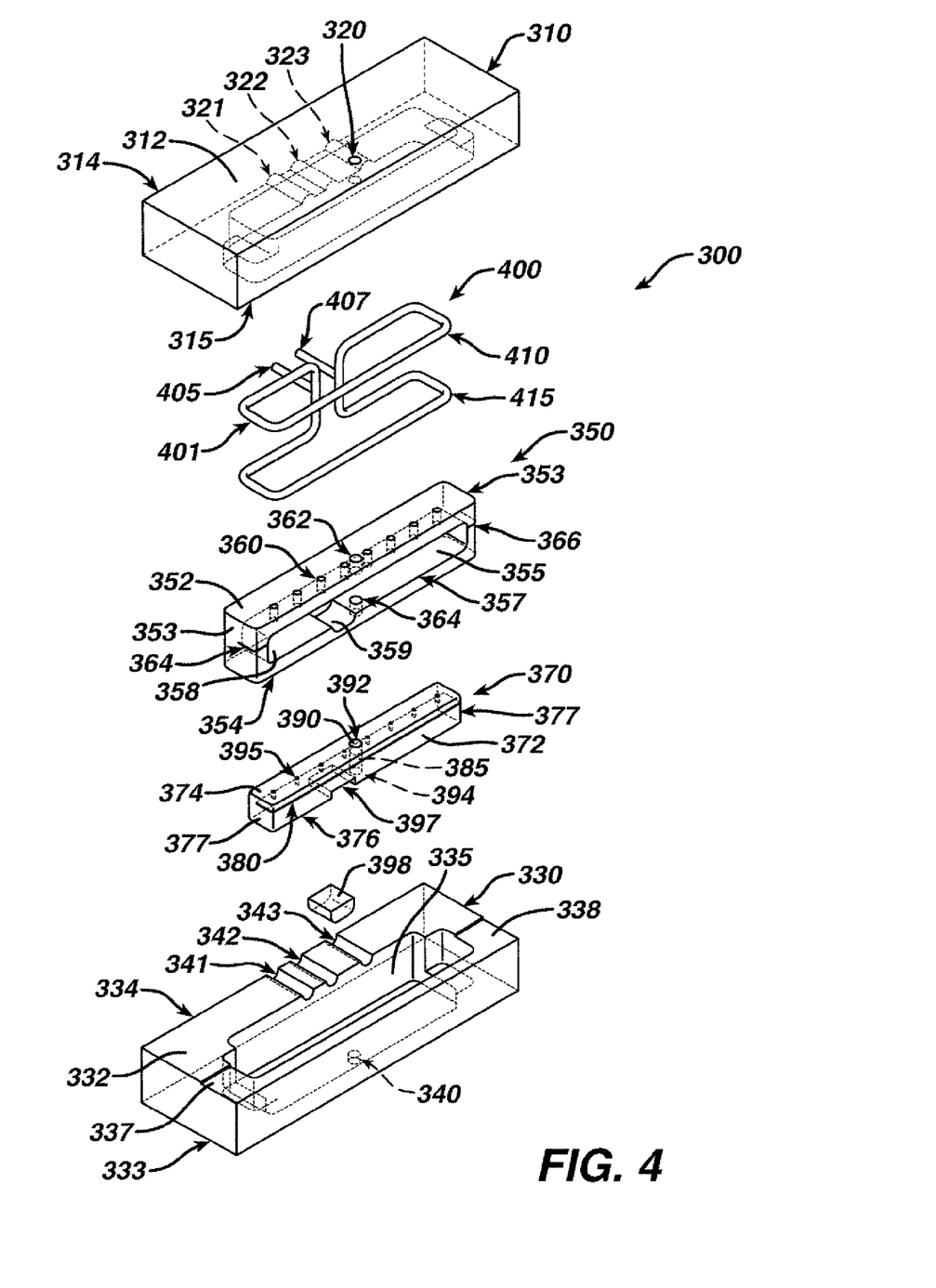
FIG. 4 is an exploded perspective view of a heating fixture useful in the practice of the process of the present invention to heat needle blanks.
Figure 5:
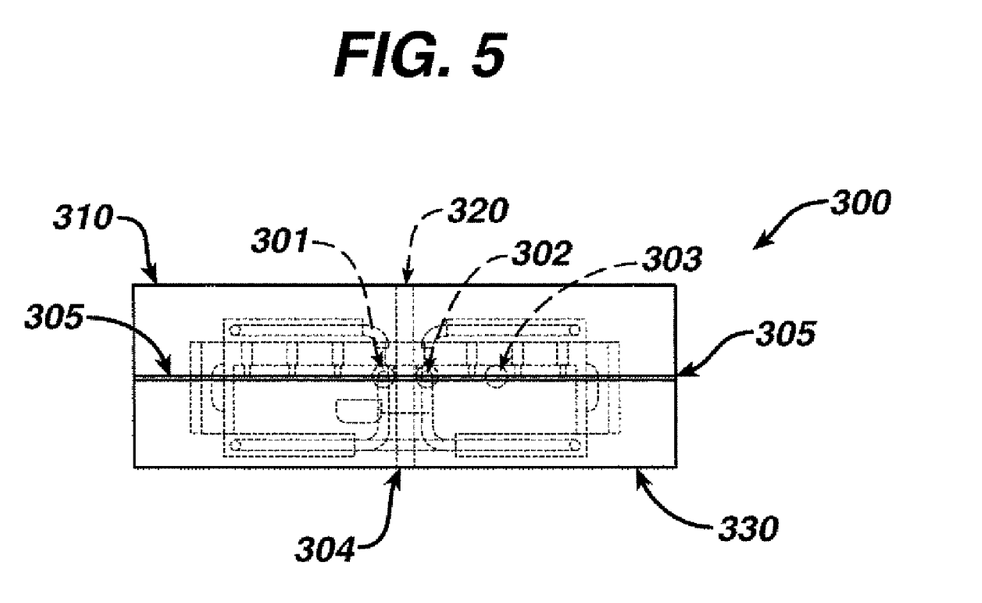
FIG. 5 illustrates a side view of the heating fixture of FIG. 4 assembled.
Figure 6:
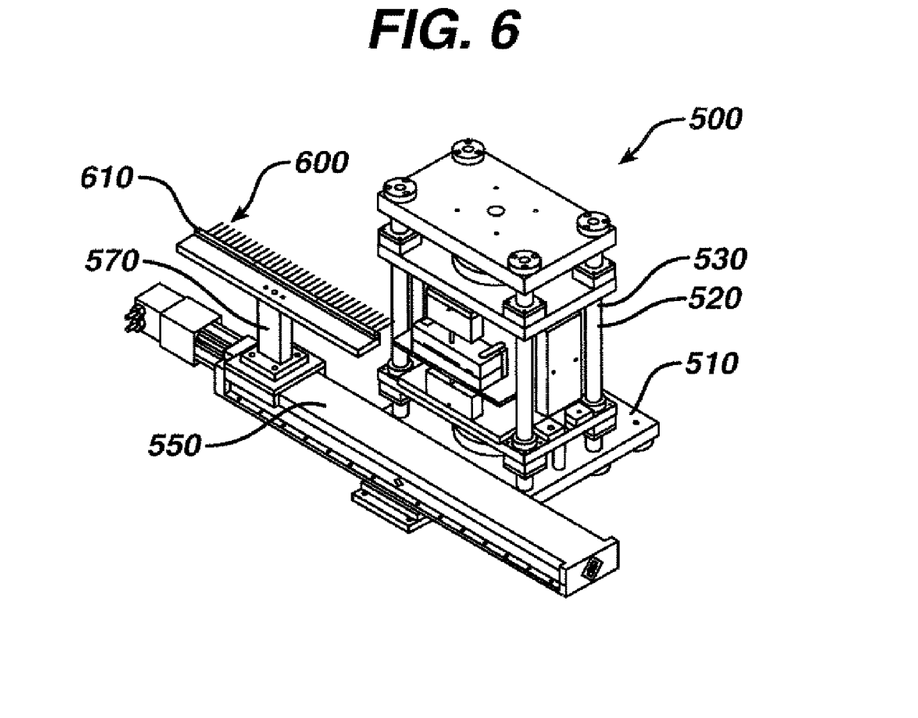
FIG. 6 illustrates a perspective view of a machine used to manufacture alloy surgical needles; the heating fixture of FIG. 4 is mounted therein.
Figure 7:
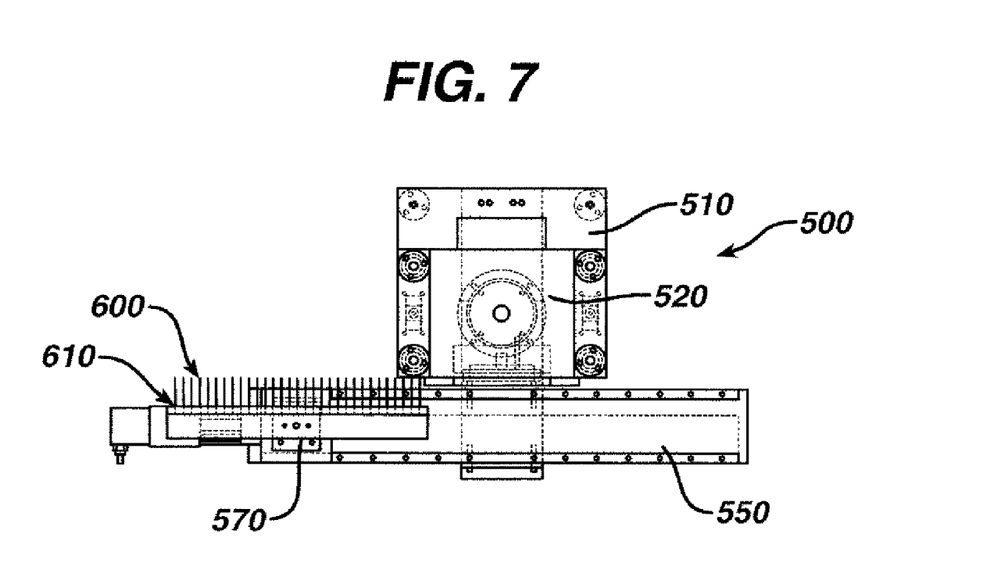
FIG. 7 is a top view of the machine of FIG. 6.
Figure 8:
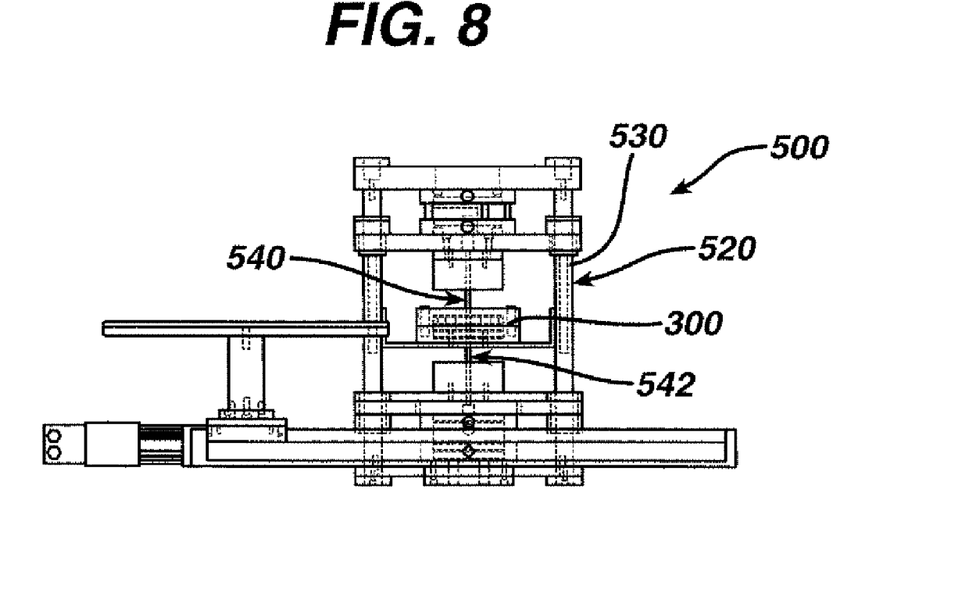
FIG. 8 is a front view of the machine of FIG. 6.
Figure 9:
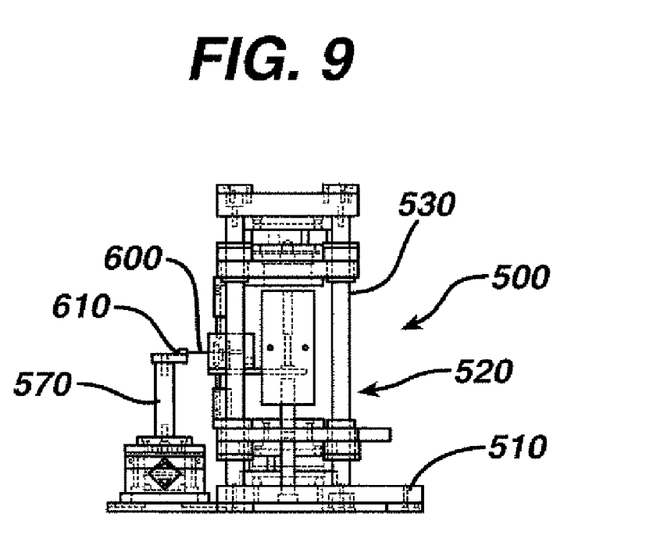
FIG. 9 is an end view of the machine of FIG. 6

Referring now to FIGS. 4 and 5 an inductively coupled heating fixture 300 useful in the process of the present invention is illustrated. Heating fixture 300 is seen to have top insulator member 310 and bottom insulator member 330. Insulator members 310 and 330 are seen to have inner cavities 315 and 335 respectively. Insulator member 310 is seen to have die passage opening 320 extending through top 312; opening 320 is in communication with cavity 315. The semi-circular grooves 321, 322 and 323 are seen to extend from the rear side 314 to the interior cavity 315. Similarly, bottom insulator 330 is seen to have die passage opening 340 extending through bottom 333; opening 340 is in communication with interior cavity 335. The semi-circular grooves 341, 342 and 343 are seen to extend from the rear side 334 to the interior cavity 335. When assembled, the grooves 321, 322, and 323 align with grooves 341, 342 and 343 to form passages 301 and 302 for the RF source and passage 303 for the shielding gas. The bottom insulator member 330 is also seen to have top surface 332 and steps 337 adjoining lower slot surface 338. The insulator block member 350 is seen to have top 352 and cavity 355 extending therein with lateral opening 357. A plurality of gas ports 360 extend from the top 352 into and in communication with cavity 355. A die passage 362 extends from the top 352 into cavity 355. Similarly, a die passage 364 extends from the bottom 354 into cavity 355. The opposed needle slots 366 are seen to be contained in opposing ends 353 of member 350. Also contained in member 350 is a keyway slot 359 extending from the bottom interior wall 358 of cavity 355. The metal heater element 370 is seen to be contained with the cavity 355 of insulator block member 350. The heater element 370 is seen to have slot 380 extending into the front side 372 of heater element 370. Slot 380 extends into opposed ends 377 of heater element 370. Extending through the heater element 370 is the die passage 390 having top passage 392 and bottom passage 394. Die passage 390 is seen to intersect slot 380. A plurality of gas flow passages 395 are seen to extend down from the top 374 of heater element 370 into slot 380. The keyway slot 397 is seen to be contained in the bottom 376 of heater element 370 to receive the key member 398. The RF induction source 400 is seen to be a tubular conductive member 401 having an inlet 405 and an outlet 407. The member 401 is bent to have an upper section 410 and a bottom section 415 such that the metal heater element 370 and the insulator block member 350 are contained between the two sections when the heating fixture 300 is assembled.

A side view of the heating fixture 300 is seen in FIG. 5. In order to assemble the fixture 300, the metal heater element 370 is place within cavity 355 of insulator block 350 such that the slot 380 is facing outward. The key member 398 is then inserted into the keyway slot 397 and the keyway slot 359 locking heater element 370 into cavity 355. Next, the insulator block 350 containing keyed-in heater element 370 is place between the upper section 410 and the bottom section 415 of RF induction source 400. Then this sub assembly is placed into the cavity 335 of bottom member 330. The assembly of the fixture 300 is completed by mounting top insulating member 310 to bottom member 330, such that the upper section 410 of member 410 and the upper section of insulating block 350 are contained within the cavity 315. As seen in FIG. 5, the assembled fixture 300 is seen to have slot 305 resulting from steps 337 and lower terraced surface 338. Slot 305 is in communication with slots 366 of insulator block 350 and slot 380 of heater element 370. The fixture 300 is mounted to a conventional die press. In operation, the RF induction source 400 is connected to an RF generator. The RF magnetic field generated by the induction source 400 couples with the heating element 370 invoking an internal RF current that in turn resistively heats the element 370. Needle blanks are fed through the slots 305, 366, and 380 in the fixture 300 in an indexed manner. While in the slot 380 contained in heater element 370, surgical needle blanks are heated by convection and radiation to the desired temperature prior to moving to a die striking location within the intersection 385 of slot 380 and die passage 390 between the die passages 392 and 394 and maintained at that temperature while at the die striking location. When indexed to the intersection 385, upper and lower dies 540 and 542 strike the needle blanks 610 to produce the desired needle body shape, needle point shape or suture receiving channel. During the processing, a shielding gas is optionally connected to the gas port 303 in the insulating blocks 310 and 330.

Referring now to FIGS. 6-9, a needle processing machine 500 is seen. The machine 500 is seen to have frame 510. Mounted to the frame 510 are the die press apparatus 520 and the feeder rail 550. Slidably mounted to feeder rail 550 is the indexing needle blank fixture 570. A plurality of needle blanks 600 is mounted to a carrier strip 610. Carrier strip 610 is mounted to the fixture 570 such that the needle blanks are facing toward the die press apparatus 520. Mounted to the frame 530 of the die press apparatus 520 is the heating fixture 300. Also mounted to the frame 530 are the upper die 540 and the lower die 542. In operation, refractory metal alloy needle blanks 600 are pre-mounted to a carrier strip 610. The strip 610 containing the needle blanks 600 is mounted to the fixture 570. The optional shielding gas is connected to gas port opening 303 in the fixture 300 such that the shielding gas is flowing through ports 362 and 395 in the insulator block 350 and heater element 370 and exiting through slot 380 in heater element 370, slots 366 in insulating block 350, and slot 305 between insulating members 310 and 330. The RF generator connected to the RF induction source 400 is energized, causing RF source 400 to emit RF radiation which inductively heats up heater element 370. The fixture 570 is then moved by a conventional index controller and mechanism such that needles blanks 600 are moved through the slots 305, 366 and 380 and to a die striking position 385 in slot 380. The residence time in the slot 380 of the heater element is sufficient to effectively heat each needle blank 600 to a temperature above the ductile to brittle transition temperature but below the re-crystallization temperature prior to and during the die forming operation. The upper and lower dies 540 and 542 are then moved through the die passages and sufficient force is exerted upon the needle blank by the dies to effectively form the needle blank into the desired configuration. The index process continues until all of the needle blanks 600 on the carrier strip 610 have been formed. The optional shielding gases useful with the machine 500 and fixture 300 include: argon, hydrogen, helium, neon, carbon dioxide, $CO/CO_2$ mixtures, combinations of the aforementioned and the like. The RF generator coupled to the RF source 400 will be a conventional generator producing a sufficiently effective frequency, e.g., in the range of about 1 kilohertz to 10 Megahertz and having a sufficiently effective power output, e.g., about 1 to 100 kilowatts. The choice of a suitable generator, frequency range and power output will depend upon various factors including the size of the RF source, the size and shape and material of construction of the heating element, and the residence time in the slot of the heating element, I.e., the indexing speed. The heater block may be made of conventional metals and metal alloys such as nickel-based, molybdenum-based, or tungsten-based alloys. The insulating members and insulator block may be made from conventional insulating materials such as ceramic fiber insulation.

As an additional benefit associated with the novel thermal forming methods of the present invention, alloys that may exhibit high DBTT can be formed into suture needles. For example, in the W—Re alloy system, alloys with high rhenium concentrations tend to have lower DBTT than alloys with low rhenium concentration. However, from a commercial perspective, rhenium has a high raw material cost and can be an exceedingly expensive component of the alloy. If the thermal forming methods of the present invention are used, low rhenium concentrations may be used in lieu of high rhenium concentrations to realize a substantial cost savings. An additional benefit is that the market price for the finished suture needle may in theory be reduced, as raw material costs no longer need to be passed on to the customer, and use of the tungsten alloys as suture needle materials may be expanded to a greater number of needle designs.

Furthermore, greater tolerances for impurities in the alloy (that have the effect of elevating the DBTT) may be permissible if the thermal forming methods of the present invention are used. Yet another associated benefit is that supplier availability may broaden, thereby possibly resulting in decreased material cost.

Still yet an additional benefit of use of the novel methods of the present is seen when a needle blank is curved to form a curved or arcuate suture needle with the shape or configuration of, for example, a, ⅜, or circle. During the conventional needle curving process performed at room temperature, residual stresses are typically imparted to the needle body that detrimentally impact the yield bend moment of the needle. It is believed that heat treatment after the curving operation eliminates some or all of such residual stresses and substantially enhances the yielding bend moment of the needle. Thermal forming operations to curve the suture needle at elevated temperatures (e.g. in excess of 900° C.) may result in a similar improvement in yield bend moment.

Heat treating methods for the coloration of refractory alloy suture needles via the formation of a thin native surface oxide may be applied in conjunction with the in situ thermal forming methods of the present invention. Refractory alloy suture needles may thus be colored during needle manufacturing operations, thus eliminating the need for a subsequent thermal coloring step. Where coloration is a desired outcome, the use of a conventional shielding gas should be avoided, or used in combination with a conventional oxidizing gas However, if coloration is not desired, a shielding gas may be used.

The following examples are illustrative of the principles and practice of the present invention, although not limited thereto.

Example 1

Needle blanks comprised of a tungsten-26% rhenium alloy with a nominal starting wire diameter of 0.203 mm were pressed between two opposing carbide dies to produce parallel opposed body flats. The tungsten-26% rhenium material from which the needle blank was made was acquired from Toshiba Corporation (Yokohama, Japan) and exhibited a breaking strength of 3450 MPa in wire form. A conventional pneumatic uniaxial press was used for the experiments with flat carbide dies. The length of the needle blank, over which body flats were formed, was at least 1 cm. In one set of experiments the needle blanks were pressed to various thicknesses at room temperature and visually examined for cracks at 30× magnification with a stereoscope. It was found that cracks could be formed longitudinally along the length of the wire when the body flat was coined to a thickness equal to or less than ~0.175 mm. In a parallel set of experiments, the W-26% Re needle blanks were resistively heated immediately prior to and during the pressing operation using the experimental configuration similar to that depicted in FIG. 1. A conventional AC variac was used to sufficiently deliver and adjust the current through the needle blank. In this way the needle could be effectively heated to above 1000° C. as evidenced by the yellow to white glow that was produced. The entire heating and pressing operation took ~1.5 seconds. Visual examination at 30× magnification was used to detect cracks. It was found that needles that were heated to above ~1000° C. (yellow to white glow discharge) could be produced with body flats of 0.15 mm or less without any visually detectable cracks.

Example 2

In order to assess the ductility of the suture needles of Example 1, a reshape test was performed wherein each needle was held near its proximal end with suitable, conventional needle holders and bent back and forth through 180 degrees multiple times until fracture of the needle occurred. Each bend though 90 degrees from the initial shape of the needle was given a ½ count. The total number of counts is a measure of ductility with the higher numbers indicating greater ductility. Most suture needles are required by their manufacturers to exhibit a reshape value of at least 1.0. The W-26% Re suture needles made in Example 1 above exhibited reshape values in excess of 4.0 thereby meeting and exceeding the standard requirement.

The novel methods of the present invention for thermoforming surgical needles have numerous advantages and benefits. These advantages and benefits include: production of refractory alloy suture needles with flattened or I-beam body sections, coined needle points, and suture receiving channels without cracking or splitting the needle blank and without compromising ductility and toughness of the suture needle, improved resistance to bending, stiffness, and strength via thermal curving of the suture needle, coloration of the needle surface via native surface oxide formation in situ during thermal forming negating the need for subsequent coloration processes, and selection of lower cost refractory alloys with high DBTT.

Although this invention has been shown and described with respect to detailed embodiments thereof it will be understood by those skilled in the art that various changes in form and detail thereof may be made without departing from the spirit and scope of the claimed invention.

We claim:

1. A method of forming a refractory alloy into a surgical needle, said method comprising:
   providing an alloy metal needle blank, said needle blank comprising a refractory metal alloy;
   providing a heating fixture, the heating fixture comprising:
      an upper insulating member having a top side, a bottom side and a cavity extending up from the bottom side, the member having a die passage extending therethrough for receiving a die;
      a lower insulating member having a top side, a bottom side and a cavity extending down from the top side, the member having a die passage extending therethrough for receiving a die;
      an insulator block having a cavity and a pair of opposed needle slots, the block having a passage extending therethrough for receiving at least one die;
      a heater element block mounted in the cavity of the insulator block, said heater element block having a longitudinal needle slot substantially in alignment with the opposed slots of the insulator block, said heater element block having a die passage extending therethrough and intersecting the slot for receiving at least one die; and, a RF induction source member, wherein the insulator block containing the heater element and the RF induction source member are mounted in the cavities between the upper and lower insulating members to form an inductive heating fixture such that there is a slot between the upper and lower insulating members in alignment with the opposed slots of the insulating block and the slot of the heater element block, and such that the die passages of the lower insulating member, the insulating block, the heater element, and the upper insulating member are substantially in alignment;

heating at least a section of the needle blank to a temperature above the ductile to a brittle transition temperature, but below the recrystallization temperature of the alloy; and, mechanically forming the needle blank into a surgical needle.

2. The method of claim 1 wherein the temperature is between about 100° C. to about 1600° C.

3. The method of claim 1 wherein the temperature is between about 600° C. and about 1400° C.

4. The method of claim 1 wherein the elongation to break of the alloy is increased to exceed 5%.

5. The method of claim 1 wherein the forming operation is selected from the group consisting of needle body forming, needle point coining, needle channel coining, and needle curving.

6. The method of claim 1 wherein the alloy has a Rhenium concentration comprising of about 0% to about 30%

7. The method of claim 1 wherein the needle is heated using hot gas jets.

8. The method of claim 1 wherein the needle is heated using a resistive heating element.

9. The method of claim 1 wherein the needle is heated by contacting electrodes to the needle blank and causing an electrical current to flow through the needle blank.

10. The method of claim 1 wherein the needle is in an oxygen free atmosphere when at an elevated temperature.

11. The method of claim 10 wherein the oxygen free atmosphere is a shielding gas or combination of shielding gases selected from the group consisting of nitrogen, argon, helium, and hydrogen.

12. The method of claim 1 wherein the refractory alloy comprises Tungsten and one or more elements selected from the group consisting of Rhenium, Molybdenum, Tantalum, Titanium, Yttrium, Zirconium, and Niobium.

13. The method of claim 1 wherein the refractory alloy comprises Molybdenum and one or more elements selected from the group consisting of Rhenium, Tungsten, Tantalum, Osmium, Iridium, Yttrium, Zirconium, and Niobium.

14. The method of claim 1 wherein the refractory alloy is Tungsten-Rhenium (W—Re).

15. The method of claim 14 wherein the W—Re alloy has a rhenium concentration less than 30% and preferably 26% or less.

16. The method of claim 14 wherein the temperature of the W—Re alloy is elevated to between 100° C. and 1600° C. and more preferably between about 600° C. and 1400° C.

where the forming operation is selected from the group consisting of coining, flattening, channel forming, point forming, and curving.

17. An heating fixture for heating refractory metal alloy surgical needle blanks, comprising:

an upper insulating member having a top side, a bottom side and a cavity extending up from the bottom side, the member having a die passage extending therethrough for receiving a die;

a lower insulating member having a top side, a bottom side and a cavity extending down from the top side, the member having a die passage extending therethrough for receiving a die;

an insulator block having a cavity and a pair of opposed needle slots, the block having a passage extending therethrough for receiving at least one die;

a heater element block mounted in the cavity of the insulator block, said heater element block having a longitudinal needle slot substantially in alignment with the opposed slots of the insulator block, said heater element block having a die passage extending therethrough and intersecting the slot for receiving at least one die; and, a RF induction source member, wherein the insulator block containing the heater element and the RF induction source member are mounted in the cavities between the upper and lower insulating members to form an inductive heating fixture such that there is a slot between the upper and lower insulating members in alignment with the opposed slots of the insulating block and the slot of the heater element block, and such that the die passages of the lower insulating member, the insulating block, the heater element, and the upper insulating member are substantially in alignment.

18. The fixture of claim 17, additionally comprising at least one passage for introducing a gas flow.

19. The fixture of claim 18, wherein the insulating block and the heater element block additionally comprise at least one passage for receiving a gas flow.

20. The fixture of claim 19, wherein the gas passage of the heater element block is in communication with the heater element slot.

21. The fixture of claim 17, wherein the RF source member has an upper section and a lower section.

22. An apparatus for forming refractory alloy surgical needles, comprising:

a frame;

a die press mounted to the frame, having upper and lower dies;

an indexing fixture slidably mounted to the frame, said fixture capable of receiving and holding at least one refractory alloy needle blank;

an inductive heating fixture, said fixture comprising:

an upper insulating member having a top side, a bottom side and a cavity extending up from the bottom side, the member having a die passage extending therethrough for receiving a die;

a lower insulating member having a top side, a bottom side and a cavity extending down from the top side, the member having a die passage extending therethrough for receiving a die;

an insulator block having a cavity and a pair of opposed needle slots, the block having a passage extending therethrough for receiving at least one die;

a heater element block mounted in the cavity of the insulator block, said heater element block having a longitudinal needle slot substantially in alignment with the opposed slots of the insulator block, said heater element block having a die passage extending therethrough and intersecting the slot for receiving at least one die; and,
a RF inductive source member,
wherein the insulator block containing the the heater element and the RF source member are mounted in the cavities between the upper and lower insulating members to form an inductive heating fixture such that there is a slot between the upper and lower insulating members in alignment with the opposed slots of the insulating block and the slot of the heater element block, and such that the die passages of the lower insulating member, the insulating block, the heater element, and the upper insulating member are substantially in alignment, and,
wherein the indexing fixture moves each needle blank through the slots in the heating fixture to a location within the fixture where the upper and lower dies may contact each needle blank after each such needle blank is heated.

* * * * *